United States Patent [19]

Roman

[11] 4,052,411
[45] Oct. 4, 1977

[54] ESTERS OF DERIVATIVES OF 2-IMIDAZOLIDINYLIDENENITROACETIC ACID

[75] Inventor: Steven A. Roman, Oakdale, Calif.

[73] Assignee: Shell Oil Company, Houston, Tex.

[21] Appl. No.: 729,741

[22] Filed: Oct. 6, 1976

[51] Int. Cl.$^2$ ............................................. C07D 233/26
[52] U.S. Cl. .......................................... 548/342; 71/92
[58] Field of Search ....................................... 260/309.7

[56] References Cited

U.S. PATENT DOCUMENTS 3,948,934  4/1976  Tieman et al. .................... 260/309.7

OTHER PUBLICATIONS

Meyer et al., Chem. Abst., 1973, vol. 79, No. 146519d.

Wennerbeck, Acta Chem. Scand., 1973, vol. 27, pp. 258-270.

*Primary Examiner*—Natalie Trousof

[57] ABSTRACT

Herbicidal compounds of the formula

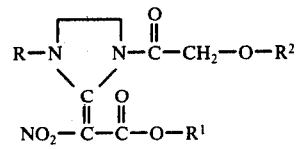

wherein R and R$^1$ each is alkyl of from one to twenty carbon atoms and R$^2$ is 2,4-dichloro-, 2-methyl-4-chloro- or 2,4,5-trichlorophenyl.

2 Claims, No Drawings

ESTERS OF DERIVATIVES OF 2-IMIDAZOLIDINYLIDENENITROACETIC ACID

DESCRIPTION OF THE INVENTION:

It has been found that useful herbicidal properties are possessed by certain esters of derivatives of 2-imidazolidinylideneenitroacetic acid, these derivatives being described by the general formula:

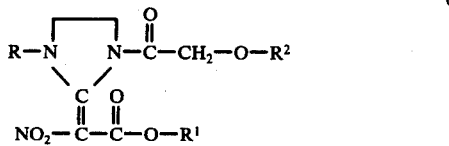

(I)

wherein R and $R^1$ each is straight-chain or branched-chain alkyl of from one to twenty carbon atoms and $R^2$ is 2,4-dichloro-, 2-methyl-4-chloro- or 2,4,5-trichloro-phenyl.

For illustration, preparation of a typical individual species of the genus defined by Formula (I) is described in the example included hereinafter. Other typical individual species of the genus are the following, wherein the respective moieties, referring to Formula (I), are:

| R | $R^1$ | $R^2$ |
|---|---|---|
| methyl | octyl | 2,4-dichlorophenyl |
| octyl | methyl | 2,4-dichlorophenyl |
| methyl | methyl | 2-methyl-4-chlorophenyl |
| methyl | methyl | 2,4,5-trichlorophenyl |

The compounds of this invention can be prepared by treating a sodium salt of a (1-R-2-imidazolidinylidene)-nitroacetic acid ester with the appropriate acid chloride,

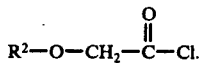

The acid chloride reactants are known compounds.

The imidazolidinylidene precursors are converted to sodium salts by treatment with sodium hydride, preferably in a suitable liquid reaction medium, such as tetrahydrofuran or dimethylformamide, at a low temperature, for example, about 0°-5° C. To enable efficient control of the often exothermic reaction, it may be found desirable to add slowly a solution or suspension of the imidazolidinylidene precursor to a stirred, cooled solution or suspension of the sodium hydride, the mixture being stirred further until hydrogen ceases to evolve. The mixture then may be allowed to warm, for example to room temperature, to ensure completion of the reaction.

Treatment of the sodium salt with the acid chloride can be effectively carried out under similar conditions: adding a suspension or solution of the acid chloride slowly to a stirred solution or suspension of the sodium salt, the reaction mixture being cooled as necessary to maintain it at a low temperature — again, suitably about 0°-5° C — then allowing the stirred mixture to warm, for example to room temperature, and stirring the warmed mixture for a period of time to ensure essentially complete reaction.

It often will be found convenient to employ the same liquid reaction medium in both steps of the process, with tetrahydrofuran or dimethylformamide generally being suitable for this purpose. In such a case, the solution or suspension of the sodium salt obtained as the product of the sodium hydride/imidazolidinylidene precursor reaction is treated directly with the solution or suspension of the acid chloride.

The desired product can be isolated from the crude reaction mixture and purified by conventional methods, such as filtration, extraction, crystallization and elution (chromatography).

Recovery of the product is most effectively attained in most cases by quenching the final reaction mixture in cold water. In some cases, the desired product can be isolated by filtering the resulting mixture. It then can be washed with water, then with a solvent such as ether, to remove residual tetrahydrofuran or dimethylformamide, and by-products, then dried and purified by crystallization form a suitable solvent. In other cases, where the product is not insoluble, it can be recovered from the quench-mixture by extracting the mixture with a suitable water-insoluble solvent, such as methylene chloride or ether.

The precursor esters of (1-R-2-imidazolidinylidene)-nitroacetic acid can be prepared by treating a 1-alkyl-2-(methylthio)-2-imidazoline with an alkyl nitroacetate in the presence of zinc chloride as catalyst (S. Zen, et al., Kogyo Kagaku Zasshi, 74, 70 (1971)). This treatment is suitably conducted by heating a stirred mixture of the imidazoline, the nitroacetate and the catalyst to a temperature of from about 85° C to about 125° C, preferably about 100°-105° C, and then recovering the desired product by conventional methods. The 1-alkyl-2-(methylthio)-2-imidazolidene precursor can be prepared by treating a 1-alkyl-imidazolidene-2-thione (method of preparation described in McKay, et al., J. Org. Chem., 22, 1581-3 (1957)) with dimethyl sulfate and then treating the resulting intermediate with sodium hydroxide, as illustrated in Example 1, following.

Preparation of these compounds is illustrated in the following example. The identities of the products and of intermediates employed were confirmed by appropriate elemental and spectral analyses.

EXAMPLE 1 methyl(1-((2,4-dichlorphenoxy)acetyl)-3-methyl-2-imidazolidinylidene)nitroacetate (1)

360 g of dimethyl sulfate was added dropwise to a stirred and refluxing suspension of 332 g of 1-methyl-imidazolidine-2-thione in 900 ml of hexane. After 2 hours further stirring at the same temperature, the mixture was cooled and treated with 114 g of sodium hydroxide in 320 ml of water. The hexane layer was separated and dried (MgSO$_4$). The aqueous layer was extracted with methylene chloride and the extract was dried (MgSO$_4$). The solvents were evaporated under reduced pressure and the combined residues were distilled to give 1-methyl-2-(methylthio)-2-imidazoline (1A) as a colorless liquid, b.p.: 50°-52° at 0.02 Torr.

19.5 g of 1A, 17.8 g of methyl nitroacetate and a small amount of zinc chloride were mixed and the mixture was heated to 100°-105°. After 30 minutes, the solid reaction mixture was washed with ether, then with hot methanol. The mixture was filtered to give the methyl ester of (1-methyl-2-imidazolidinylidene)nitroacetic acid (1B) as a tan solid, m.p.: 209°-210°.

2.3 g of sodium hydride was slurried in 75 ml of dimethylformamide at 5°. To that slurry, at 5°, was added 19.5 g of 1B over a 30-minute period. The stirred mixture was allowed to warm to room temperature and stirred at that temperature for one hour. The mixture then was cooled to 5° and there was added thereto a solution of 25.5 g of 2,4-dichlorophenoxyacetyl chloride in 25 ml of dimethylformamide, over a 20-minute period, the stirred mixture being held at 5°-12°. The stirred mixture was allowed to warm to room temperature and stirred at that temperature overnight. The mixture then was poured into ice water. The solid was filtered, washed with water and dried by air aspiration and ether washing to give a tan-colored solid, which on recrystallization from acetonitrile gave 1, as an off-white solid, m.p.; 191°-192° (with decomposition).

The compounds of this invention exhibit useful herbicidal activity, particularly for pre-emergent application for the control of weeds.

The pre-emergence herbicidal activity of a typical compound of this invention was evaluated by planting seeds of barnyard grass, garden cress, downy brome, wild mustard, yellow foxtail, velvet leaf, soybean, grain sorghum, cotton and wheat in soil treated with the test compound at two dosages, approximately 2 and 20 lb./acre. The planted soil was held under controlled conditions of temperature, moisture, and light for 13 to 14 days. The amount of germination was then noted and the effectiveness of the test compound was rated visually, on the basis of a 0 to 9 scale, 0 rating indicating no effect, 9 indicating death of the seedlings or no germination.

The post-emergence activity of the typical compound of this invention was evaluated by spraying 7-day old crabgrass plants, 10-day old pigweed plants, 7-day old velvet leaf plants, 7-day old downy brome plants, 10-day old wild mustard, 10-day old yellow foxtail, 10-day old grain sorghum, 14-day old cotton plants and 7-day old soybean plants to runoff with liquid formulations containing the test compound at two concentrations: 0.05% and 0.5%, respectively. The sprayed plants were held under controlled conditions for 10 to 11 days and the effect of the test compound was then evaluated visually, the results being rated on the 0 to 9 scale described above.

The test compound was found to be highly active in the pre-emergence application, giving a rating of 8 or 9 with respect to all of the species of plants, at both dosages. The compound was less active in the post-emergence application, being active (rating of 6 or higher) at the lower dosage only with respect to the pigweed, velvet leaf, mustard, cotton and soybean.

In further tests, the pre-emergent activity and broad activity spectrum of the compound of the invention was confirmed, it being active at a dosage of 0.5 lb./acre with respect to alfalfa, cotton, peanuts, rice, sorghum, soybean, sugar beet, barnyard grass, crabgrass, downy brome, fall panicum, johnson grass, cocklebur, coffeeweed, lambsquarters, morning glory, mustard, pigweed, prickly sida, sicklepod and velvet leaf. It showed some activity with respect to corn, wheat, quackgrass, wild oats, yellow foxtail and jimsonweed, and was not active with respect to giant foxtail, at that dosage.

When applied as a herbicide, a compound of the invention ordinarily is formulated with a carrier and/or a surface active agent.

By "carrier" is meant here a solid or fluid material, which may be inorganic or organic and of synthetic or natural origin, with which the herbicide is mixed or formulated to facilitate its application to the plant, seed, soil or other object to be treated, or its storage, transport or handling.

The surface-active agent my be an emulsifying agent or a dispersing agent or a wetting agent; it may be non-ionic or ionic.

Any of the carrier materials or surface-active agents usually applied in formulating pesticides may be used, and suitable examples of these are to be found, for example, in United Kingdom Pat. specification No. 1,232,930.

The compositions may be formulated as wettable powders, dusts, granules, solutions, emulsifiable concentrates, emulsions, suspension concentrates or aerosols. Wettable powders are usually compounded to contain 25, 50 or 75% w of toxicant and usually contain, in addition to solid carrier, 3-10% w of wetting and dispersing agents and, where necessary, 0-10% w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½-10% of toxicant. Granules are usually prepared to have a size between 10 and 100 BS mesh (1.676-0.152 mm), and may be manufactured by agglomeration or impregnation techniques. Generally, granules will contain ½-25% w active ingredient and 0-10% w of additives such as stabilizers, slow release modifiers and binding agents. Emulsifiable concentrates usually contain, in addition to the solvent and, when necessary, co-solvent, 10-50% w/v active ingredient, 2-20% w/v emulsifiers and 0-20% w/v or appropriate additives such as stabilizers, penetrants and corrosion inhibitors. Suspension concentrates are compounded so as to obtain a stable non-sedimenting, flowable product and usually contain 10-75% w active ingredient, 0.50-15% w of dispersing agents, 0.1-10% w of suspending agents such as protective colloids and thixotropic agents, 0-10% w of appropriate additives such as defoamers, corrosion inhibitors, stabilizers, penetrants and stickers, and as carrier, water or an organic liquid in which the active ingredient is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate with water, also are contemplated. The emulsions may be of the water-in-oil or of the oil-in-water type, and may have a thick "mayonnase"-like consistency.

The compositions may also contain other ingredients, for example, other compounds possessing pesticidal, especially insecticidal, acaricidal, herbicidal or fungicidal properties.

The amount of the herbicide of this invention necessary to kill or inhibit the growth of plants is defined as the herbicidal amount. When the compounds are used as pre-emergence herbicides, an application rate of about 0.5 to about 10 pounds per acre is used, with about 1 to about 50 pounds per acre being preferred. When the compounds are used as post-emergence herbicides, an application rate of about 1 to about 20 pounds per acre of one or more active compound per acre is used, with an application rate of about 3 to about 10 pounds per acre being preferred. This quantity will obviously vary with the individual species of herbicide, the plant species, type of formulation, environmental conditions and the like. Those versed in the herbicide field can readily determine the effective amount for a particular set of conditions.

I claim:

1. A compound of the formula:

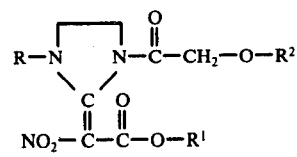

wherein R and $R^1$ each is alkyl of from one to twenty carbon atoms and $R^2$ is 2,4-dichloro-, 2-methyl-4-chloro- or 2,4,5-trichloro-phenyl.

2. A compound according to claim 1 wherein R and $R^1$ each is methyl and $R^2$ is 2,4-dichlorophenyl.

* * * * *